United States Patent [19]
Ray

[11] Patent Number: 6,042,582
[45] Date of Patent: Mar. 28, 2000

[54] INSTRUMENTATION AND METHOD FOR FACILITATING INSERTION OF SPINAL IMPLANT

[76] Inventor: Charles D. Ray, 125 Alexander Walker, Kingsmill on the James, Williamsburg, Va. 23185

[21] Appl. No.: 09/082,163

[22] Filed: May 20, 1998

Related U.S. Application Data

[60] Provisional application No. 60/047,173, May 20, 1997.

[51] Int. Cl.⁷ ................................... A61B 17/56
[52] U.S. Cl. ............................... 606/61; 623/17
[58] Field of Search ................. 606/60, 61, 62; 623/17

[56] References Cited

U.S. PATENT DOCUMENTS

| | | |
|---|---|---|
| 4,349,921 | 9/1982 | Kuntz . |
| 4,501,269 | 2/1985 | Bagby . |
| 4,545,374 | 10/1985 | Jacobson . |
| 5,122,130 | 6/1992 | Keller . |
| 5,397,330 | 3/1995 | Mikhail . |
| 5,423,825 | 6/1995 | Levine . |
| 5,431,658 | 7/1995 | Moskovich . |
| 5,484,437 | 1/1996 | Michelson . |
| 5,489,307 | 2/1996 | Kuslich et al. . |
| 5,505,732 | 4/1996 | Michelson . |
| 5,554,191 | 9/1996 | Lahille et al. ............................. 623/17 |
| 5,562,736 | 10/1996 | Ray et al. . |
| 5,571,109 | 11/1996 | Bertagnoli . |
| 5,658,336 | 8/1997 | Pisharodi ................................. 623/17 |
| 5,700,291 | 12/1997 | Kuslich et al. .......................... 623/17 |
| 5,722,977 | 3/1998 | Wilhelmy . |
| 5,797,909 | 8/1998 | Michelson ................................. 606/61 |

*Primary Examiner*—Michael Buiz
*Assistant Examiner*—Tan-Uyen Thi Ho

[57] ABSTRACT

A vertebral spacer apparatus includes an elongated member having proximal and distal end portions and defining a longitudinal axis and a vertebral spacer which is releasably mounted to the elongated member. The vertebral spacer includes an insertion end portion and a trailing end portion. The insertion end portion is configured to at least span an intervertebral space defined between adjacent vertebrae. The trailing end portion defines a dimension greater than a corresponding dimension of the insertion end portion and is sized to prevent entry thereof within the intervertebral space.

The insertion end portion preferably includes first and second opposed support surfaces wherein a dimension defined between the first and second support surfaces at least spans the intervertebral space between adjacent vertebrae. A method for implanting a fusion implant with the vertebral spacer apparatus is also disclosed.

14 Claims, 11 Drawing Sheets

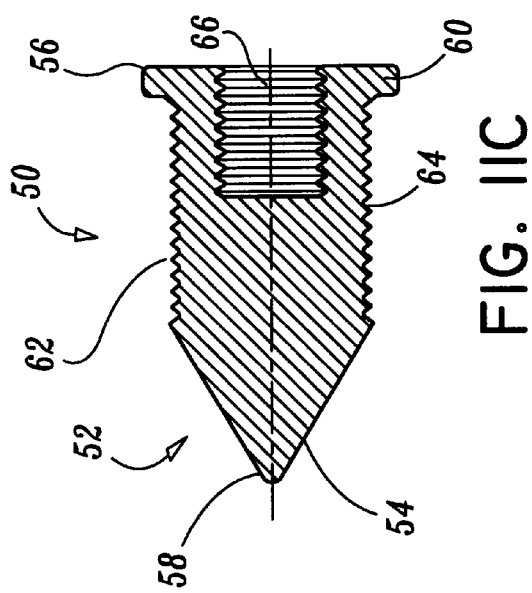
FIG. IIC
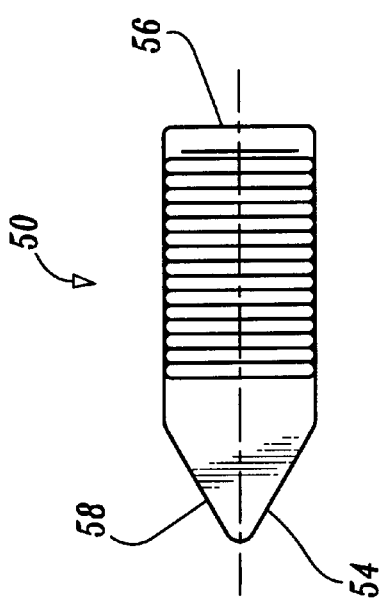
FIG. IIB
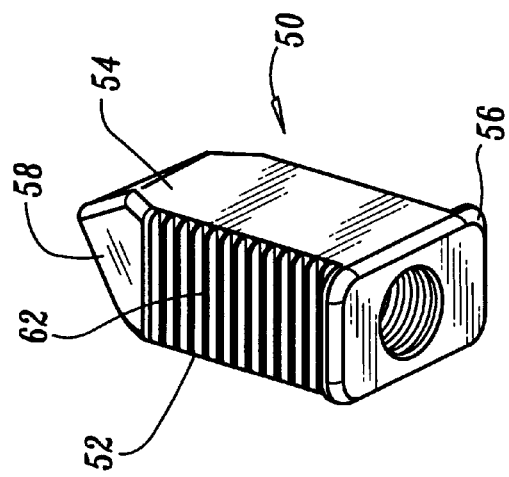
FIG. IIA

INSTRUMENTATION AND METHOD FOR FACILITATING INSERTION OF SPINAL IMPLANT

CROSS-REFERENCE TO RELATED APPLICATION(S)

This application claims priority to provisional application Ser. No. 60/047,173, filed May 20, 1997, the contents of which are incorporated herein by reference.

BACKGROUND

1. Technical Field

The present disclosure generally relates to a method and associated instrumentation for insertion of spinal implants to facilitate fusion of adjacent vertebral bodies and, more particularly, to a vertebral spacer utilized to maintain a predetermined spacial distance of adjacent vertebrae during the implant insertion.

2. Background of the Related Art

A large number of orthopedic procedures involve the insertion of either natural or prosthetic implants into bone or associated tissues. These procedures include, for example, ligament repair, joint repair or replacement, non-union fractures, facial reconstruction, spinal stabilization and spinal fusion. In a typical procedure, an insert, dowel or screw is inserted into a prepared bore formed in the bone or tissues to facilitate repair and healing. See, for example, U.S. Pat. No. 5,470,334 to Ross et al.; U.S. Pat. No. 5,454,811 to Huebner; U.S. Pat. No. 5,480,403 to Lee et al.; U.S. Pat. No. 5,358,511 to Gatturna et al.; and U.S. Pat. No. 4,877,020 to Vich.

Some implants are particularly configured with cavities and bores to facilitate bony ingrowth and enhance anchoring of the implant at the insertion site. See, for example, U.S. Pat. No. 4,328,593 to Sutter et al.; U.S. Pat. No. 4,936,851 to Fox et al.; and U.S. Pat. No. 4,878,915 to Brantigan. Other specialized implants include fusion cages having internal cavities to receive bone growth stimulation materials such as bone chips and fragments. See, for example, U.S. Pat. No. 4,501,269 to Bagby; U.S. Pat. No. 4,961,740 to Ray et al.; U.S. Pat. No. 5,015,247 to Michaelson; and U.S. Pat. No. 5,489,307 to Kuslich et al. These types of implants are particularly well suited for intervertebral spinal fusion procedures necessitated by injury, disease or some degenerative disorder of the spinal disc. Subsequently, there may be progressive degeneration leading to mechanical instability between adjacent vertebrae necessitating direct fusion of the vertebrae while maintaining a pre-defined intervertebral space. This fusion may be accomplished by the insertion of one or more of the specialized implants as discussed above and also discussed in commonly assigned U.S. Pat. No. 5,026,373, the contents of which are incorporated herein by reference.

Both anterior (transabdominal) and posterior surgical approaches are used for interbody fusions of the lumbar spine. Fusions in the cervical area of the spine are performed using an anterior or posterior approach. Typically, an implant such as a plug, dowel, prosthesis or cage is inserted into a preformed cavity or drilled bone inside the interbody, interdiscal space. Since it is desirable in these procedures to promote a "bone to bone" bridge, connective tissue and at least a portion of the distal tissue is removed. Preferably, relatively deep cuts are made in the adjacent bones in order to penetrate into the softer, more vascularized cancellous region to facilitate bone growth across the implant.

In many surgical implant techniques, two implants are inserted within the intervertebral space in side-by-side or lateral relation to fully support the adjacent vertebrae across the span of the intervertebral space. In accordance with these techniques, a first lateral side of the intervertebral space is prepared, e.g., by removing excess disc material and drilling/tapping a bore to receive the implant followed by insertion of the implant. Thereafter, the second lateral side is prepared for implant insertion in the same manner. During the initial preparation of the first lateral side of the intervertebral space, however, the adjacent vertebrae are subjected to displacement in both the lateral and longitudinal direction. This may cause additional movement of the vertebral portion disposed on the other (second) lateral side of the intervertebral space.

U.S. Pat. No. 5,489,307 to Kuslich discloses a surgical method for implanting at least two spinal implants into a disc space utilizing a solid cylindrical distraction spacer which is inserted initially within one side of the disc space. The rigid distraction spacer is intended to act against the vertebral end plates of the adjacent vertebrae to urge the vertebra apart. The spacer is sized to be fully inserted such that it is either flush or slightly recessed within the disc space.

The method and device disclosed in the Kuslich '307 patent is subject to several disadvantages which detract from its usefulness particularly in spinal surgery. For example, the Kuslich '307 distraction spacer is cylindrical thereby providing a limited area of surface contact with the adjacent vertebrae, which, consequently detracts from the stability provided to the adjacent vertebrae. Secondly, the distraction spacer is sized for complete entry within the intervertebral space, i.e., no provision is made to limit the insertion distance within the space. Consequently, over-insertion of the Kuslich distraction spacer may cause undesirable contact with, e.g., the aorta or dural nerve, depending on the surgical approach. Thirdly, the Kuslich '307 distraction spacer requires complete insertion within the intervertebral space which due to the concavity of the disc space, impedes attempts to subsequently remove the spacer after the operation.

Accordingly, the present disclosure is directed to a novel method and associated instrumentation which overcomes the disadvantages of the prior art. The novel method and instrumentation of the present disclosure facilitates the introduction of a fusion implant by stabilizing the adjacent vertebrae and providing parallel vertebral endplate distraction so as to reestablish intervertebral disc space height during implant insertion and/or the performance of other spinal procedures.

SUMMARY

Generally, the present disclosure is directed to a vertebral spacer apparatus including an elongated member having proximal and distal end portions and defining a longitudinal axis and a vertebral spacer releasably mounted to the elongated member. The vertebral spacer includes an insertion end portion and a trailing end portion. The insertion end portion is configured to at least span an intervertebral space defined between adjacent vertebrae. The trailing end portion defines a dimension greater than a corresponding dimension of the insertion end portion and is sized to prevent entry thereof within the intervertebral space.

In a preferred embodiment, the insertion end portion of the vertebral spacer includes first and second supporting surfaces for respectively engaging the adjacent vertebrae, wherein a dimension defined between the first and second supporting surfaces is sufficient to at least span an intervertebral space defined between adjacent vertebrae. The first and second supporting surfaces may be substantially planar and are preferably in general parallel relation to the longitudinal axis of the elongated member.

The trailing end portion may define a rectilinear cross-section.

Alternatively, the insertion end portion may include first and second spacer arms extending in a general longitudinal direction and being dimensioned and configured such that each spacer arm at least spans an intervertebral space defined between adjacent vertebrae. Each spacer arm may define first and second supporting surfaces for respectively engaging the adjacent vertebrae. Preferably, each spacer arm defines a dimension between the first and second supporting surfaces sufficient to contact the opposed end faces of the adjacent vertebrae upon insertion thereof.

The first and second supporting surfaces of each spacer arm are substantially planar and in general parallel relation to the longitudinal axis of the elongated member.

A method for performing a surgical procedure adjacent an intervertebral space defined between adjacent vertebrae with the vertebral spacer apparatus is also disclosed.

BRIEF DESCRIPTION OF THE DRAWINGS

Preferred embodiments of the disclosure are described hereinbelow with reference to the drawings wherein:

FIGS. 11A–11C illustrate an alternate embodiment of the vertebral spacer.

DETAILED DESCRIPTION OF THE PREFERRED EMBODIMENT(S)

The preferred embodiments of the method and instrumentation disclosed herein are discussed in terms of orthopedic spinal fusion procedures and instrumentation. It is also envisioned, however, that the disclosure is applicable to a wide variety of procedures including, but, not limited to ligament repair, joint repair or replacement, non-union fractures, facial reconstruction and spinal stabilization. In addition, it is believed that the present method and instrumentation finds application in both open and minimally invasive procedures including endoscopic and arthroscopic procedures wherein access to the surgical site is achieved through a cannula or small incision.

The following discussion will include a description of each instrument utilized in performing a spinal fusion method followed by a description of the preferred method for spinal fusion utilizing the instrumentation in accordance with the present disclosure.

In the discussion which follows, the term "proximal", as is traditional, will refer to the portion of the structure which is closest to the operator, while the term "distal" will refer to the portion which is furthest from the operator.

Figure 1:
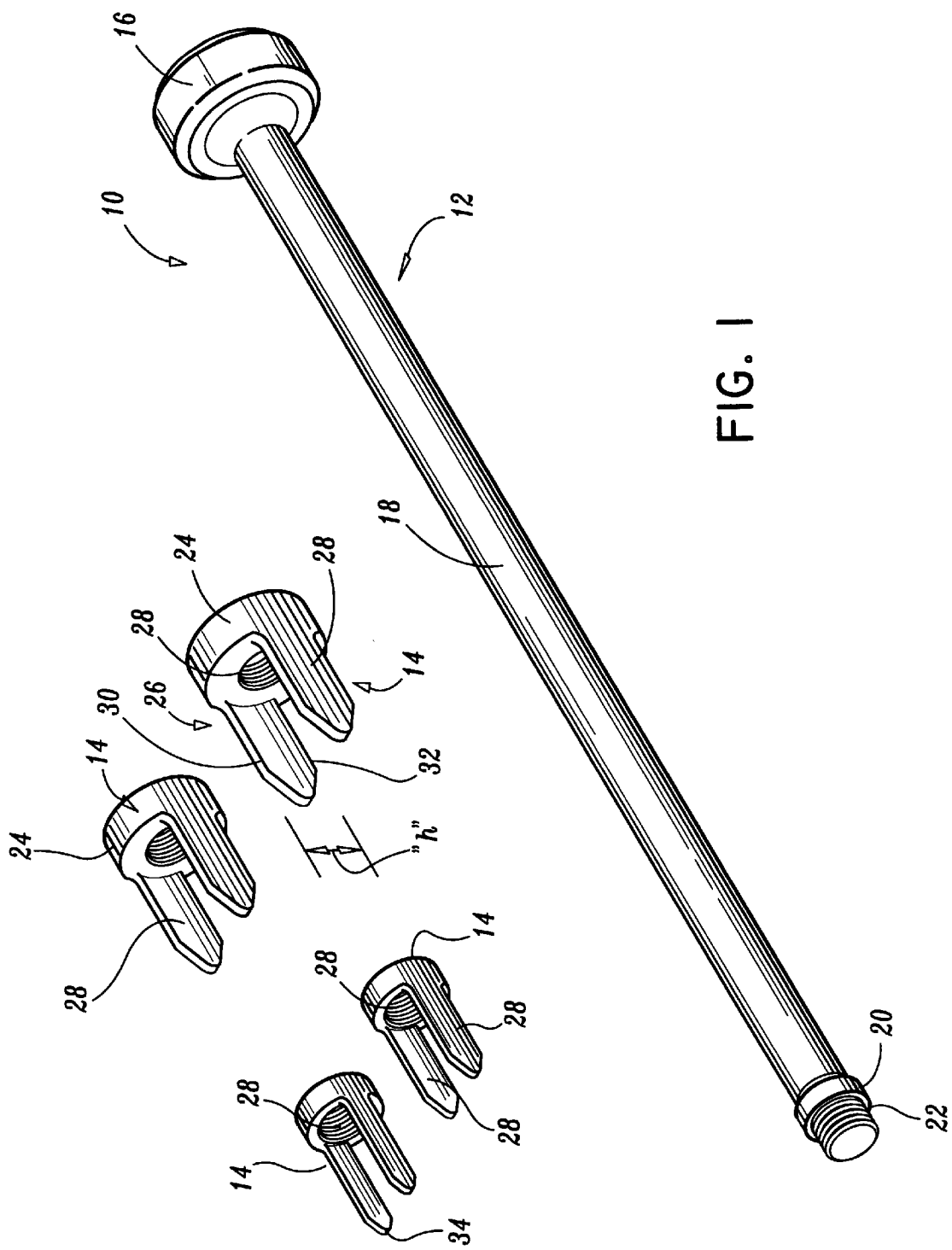
FIG. 1 illustrates a vertebral spacer apparatus and different size vertebral spacers constructed in accordance with the principles of the present disclosure and utilized in stabilizing and distracting adjacent bony structures particularly adjacent vertebrae.

Referring now to the drawings in which like reference numerals identify similar or identical elements throughout the several views, FIG. 1 illustrates in perspective view the spacer apparatus of the present disclosure. Spacer apparatus 10 includes spacer insertion instrument 12 and a vertebral spacer 14 which is detachably mounted to the insertion instrument 12. In FIG. 1, a multitude of vertebral spacers 14 (e.g., 4) are shown with each spacer 14 being of different size thus representing a kit, i.e., the spacer apparatus may be packaged with at least four vertebral spacers 14 including four diameters (for example, 12 mm, 14 mm, 16 mm and 18 mm) to correspond to the selected spinal implant size.

With continued reference to FIG. 1, insertion instrument 12 includes handle 16 and elongated portion 18 connected to the handle and extending distally therefrom. Handle 16 is generally disc-shaped as shown although other designs are contemplated as well. Elongated portion 18 defines collar 20 and threaded portion 22 adjacent its distal end. Threaded portion 22 functions in mounting vertebral spacer 14 to instrument 12.

Figure 2A:
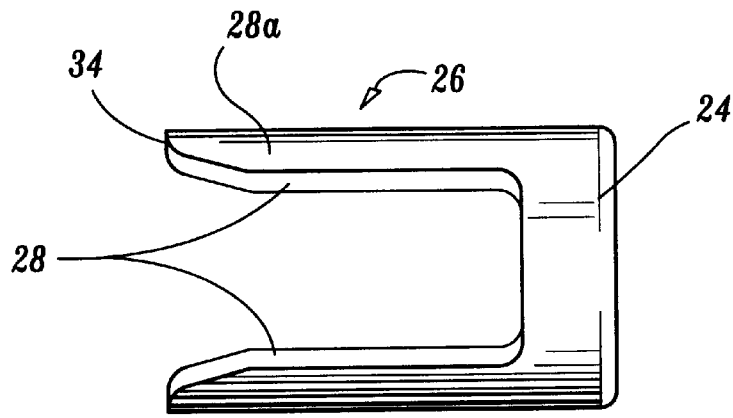
FIGS. 2A, 2B and 2C are top, side plan and front axial views respectively of the vertebral spacer of FIG. 1.
Figure 2B:
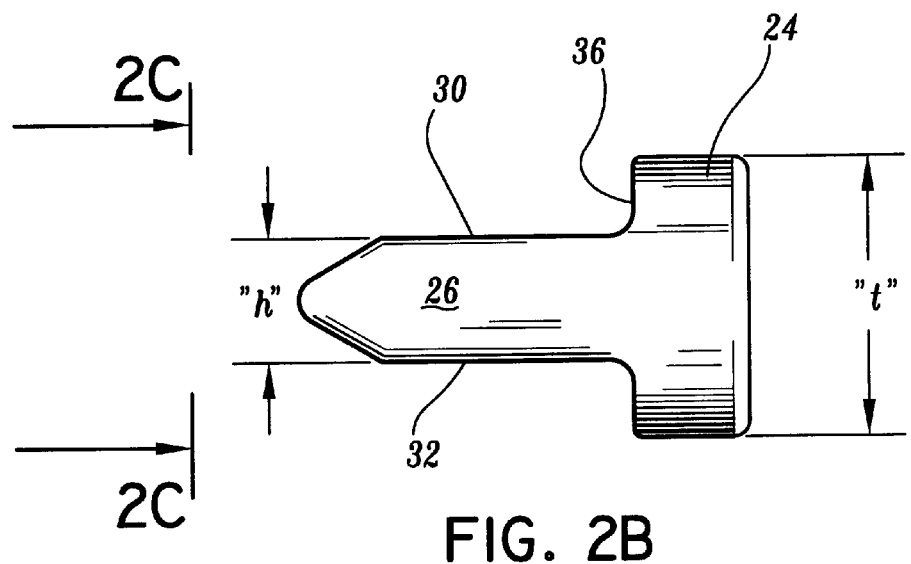
Figure 2C:
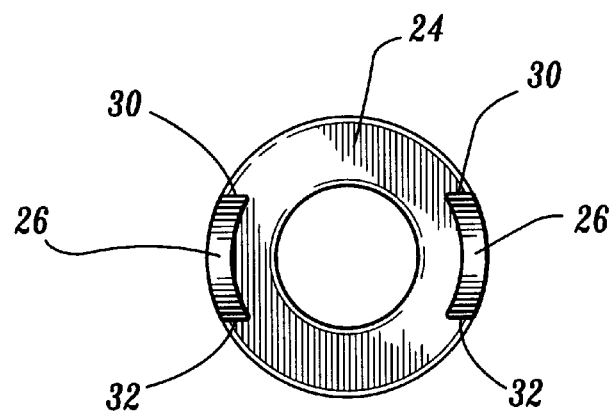

Referring now to FIGS. 2A–2C, each vertebral spacer 16 includes trailing end portion 24 and insertion end portion 26 extending distally from the trailing end portion 24. Trailing end portion 24 preferably defines a general circular cross-section which is enlarged relative to the dimension of the insertion end portion 26 and relative to the intervertebral space in which insertion end portion 26 is to be inserted. In particular, trailing end portion 24 defines a cross-sectional dimension or height "t" greater than the height of the intervertebral space, thus, precluding entry of the trailing end portion within the area of the intervertebral space. This prevents over insertion of vertebral spacer 14 within the intervertebral spacer, thereby precluding the possibility of undesired contact with the aorta and with the dural nerve. The enlarged configuration of trailing end portion 24 also facilitates removal of the vertebral spacer 14 subsequent to implant insertion. Trailing end portion 24 further defines an internal threaded bore 28 which cooperatively engages the outer threaded portion 22 of insertion instrument 12 to releasably mount vertebral spacer 16 to the insertion instrument 12. Other means for mounting vertebral spacer 16 to insertion instrument 12 are envisioned as well such as a tongue and groove arrangement, a bayonet coupling, etc.

Insertion end portion 26 preferably includes first and second diametrically opposed spacer arms 28. The outer surface 28a of each arm 28 is arcuate, i.e., defining a radius of curvature substantially equivalent to the radius of curvature of trailing end portion 24. Each arm 28 further defines first and second supporting surfaces 30, 32 which are in general parallel relation to each other and are preferably planar surfaces. The height "h" of each arm (i.e., the distance between supporting surfaces 30, 32) preferably approximates the height of the intervertebral space in which the vertebral spacer 16 is to be implanted. For example, in spinal fusion, the height "h" of each arm may be 6 mm, 8 mm, 10 mm and 12 mm. The particular vertebral spacer size is selected dependent upon the intervertebral space in which it is to be inserted. Each arm 28 further includes tapered end portions 34 defining a generally V-shaped configuration. End portion 34 facilitates insertion of retractor arms 28 within the operative site, e.g., within the intervertebral space. As noted above, the height "h" of spacer arms 28 is substantially less than corresponding height "t" (cross-sectional dimension) of trailing end portion 24, i.e., the diameter of trailing end portion 24 may be, e.g., 12 mm, 14 mm, 16 mm and 18 mm, thus defining an abutment surface 36 at the juncture of the trailing and insertion end portions 24, 26.

Figure 3:
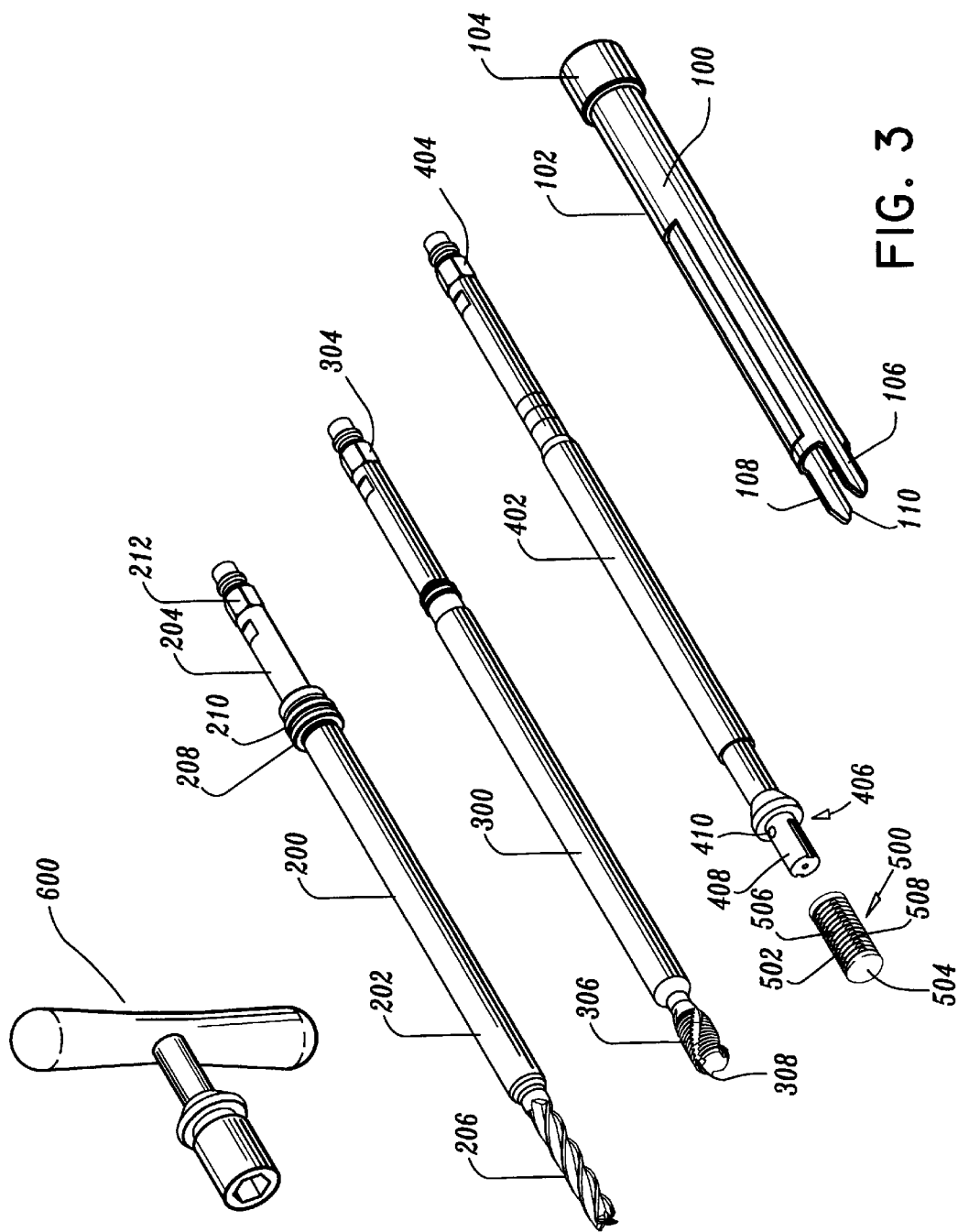
FIG. 3 is a perspective view of a surgical kit utilized for insertion of a fusion implant including, from bottom to top, a surgical retractor, an implant insertion instrument and fusion implant, a tap instrument, a drill instrument and a T-shaped handle.

Referring now to FIG. 3, the various other instruments contemplated for use in the spinal fusion procedure are illustrated and consist of surgical retractor 100, surgical drill 200, surgical tap instrument 300, implant insertion instrument 400 with implant 500 and T-shaped handle 600. Surgical retractor 100 is disclosed in commonly assigned U.S. patent application Ser. No. 08/615,379, filed Mar. 14, 1996, the contents of which are incorporated herein by reference. Retractor 100 is configured for distracting adjacent vertebral bodies to facilitate the insertion and application of an implant, for providing a cannula for insertion of the instrument, and for ensuring proper alignment of the instrumentation and accurate insertion of the implant. Retractor 100 includes sleeve 102 with an enlarged head 104 at the proximal end of the sleeve 102. Sleeve 102 includes first and second diametrically opposed retractor arms 106 having first and second parallel vertebrae supporting surfaces 108, 110.

Drill instrument 200 is also disclosed in the '379 application. Drill instrument 200 includes drill shaft 202, extension shaft 204 and drill bit 206 mounted at the distal end of the drill shaft. Extension shaft 204 has first and second collars 208, 210 which cooperate to control the depth of penetration of drill shaft 202 and drill bit 206 into the adjacent vertebrae. Drill shaft 202 includes a hexagonal-shaped head 212 at its proximal end to mount T-handle 600.

Tap instrument 300 is also disclosed in the '379 application. Tap instrument 300 is utilized for forming an internal thread within the drilled bore formed by the drill instrument. Tap instrument 300 includes elongated member 302 having hex head 304 at its proximal end to engage T-shaped handle 600. Tap instrument 300 further includes distal tapping threaded portion 306. Distal tapping portion 306 includes a plurality of conveyance channels (one is shown) 308 extending longitudinally through the cutting thread. Each conveyance channel 308 has a directional component parallel to the longitudinal axis and a directional component transverse to the longitudinal axis. Each conveyance channel 308 encompasses approximately an arc of about ⅓ the outer circumference of the tapping portion 306. Conveyance channels 308 are each dimensioned to receive bone material deburred by the cutting edges during the tapping procedure and to continually transmit the bone material proximally through the channel to avoid undesired material build up at the tapping site. In this manner, tapping instrument 300 may be used to completely tap the internal thread within the bore without interruption of the tapping procedure. It should be noted that the tap need not be used if a self-tapping implant is utilized.

Implant insertion instrument 400 includes elongated member 402 having proximal mounting portion 404 for facilitating mounting to T-shaped handle 600 and distal portion 406 which mounts implant 500. Distal portion 406 includes cylindrical mount 408 which is received within the bore of the implant 500 and implant engaging ball 410 which is received within an aperture defined in the wall of the implant 500 to fix the implant to the instrument.

Implant 500 is uniquely designed for use in spinal fusion procedures. This implant 500 is generally disclosed in U.S. Pat. No. 5,026,373 to Ray, the contents of which have been previously incorporated herein by reference, and is commonly referred to as a "fusion cage".

Implant or fusion cage 500 includes a cylindrical cage body 502 having an internal cavity or hole for accommodating bone-growth inducing substances. One end 504 of cage body 502 is closed and defines a rounded or bull-nosed configuration to facilitate insertion of the fusion cage relative to one or more bony structures. The other end defines an opening which communicates with the internal cavity. The outer surface of the cage body 502 includes a single continuous thread 506 (preferably V-shaped) having a plurality of raised turns with valleys defined between adjacent turns.

A plurality of perforations 508 are disposed within the threads and extend through the outer surface of the cage body 502 to provide direct communication between the outer surface and internal cavity 504. The perforations 508 permit immediate contact between the bone growth inducing substances within the inner cavity and the bone structure when the cage body 502 is mated to the bone structure, e.g., adjacent vertebrae. An end cap (not shown) may be mountable to the open end of cage body 502 to enclose the bone-growth inducing substances within the interior cavity.

T-shaped handle 600 includes mounting portion 602 defining hexagonal-shaped recess 604 which receives the corresponding structure of drill instrument 200, tap instrument 300 and implant insertion instrument 400.

Application of Instrumentation

The use of the instrumentation in conjunction with the insertion of the fusion cage 500 into an intervertebral space defined between adjacent vertebrae will be described. The subsequent description will be particularly focused on an open posterior spinal fusion procedure, however, it is to be appreciated that an anterior approach is contemplated as well.

Figure 4:
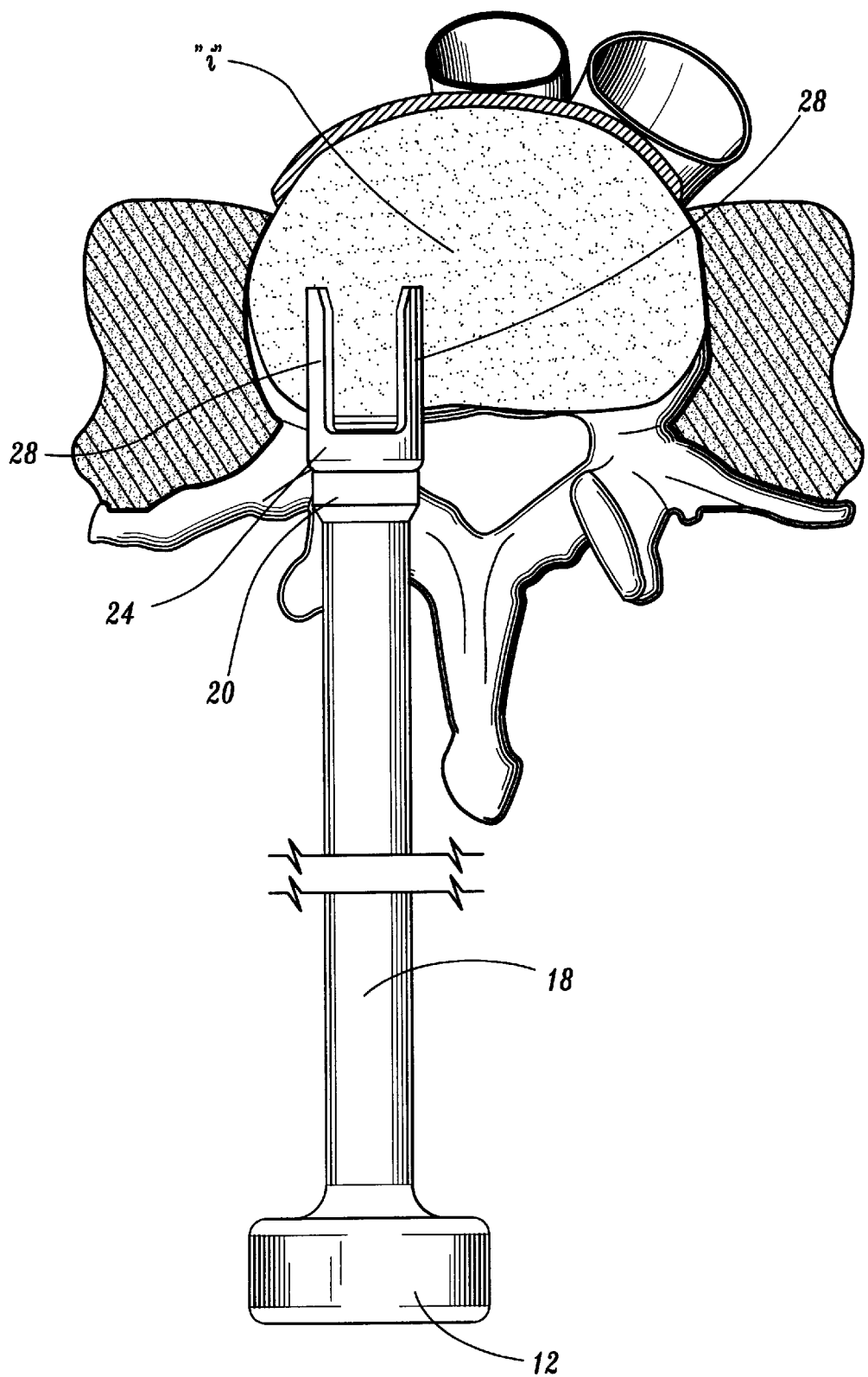
FIG. 4 is a top cross-sectional view of an intervertebral space defined between adjacent vertebrae illustrating the insertion of the vertebral spacer apparatus of FIG. 1 into the space.
Figure 5:
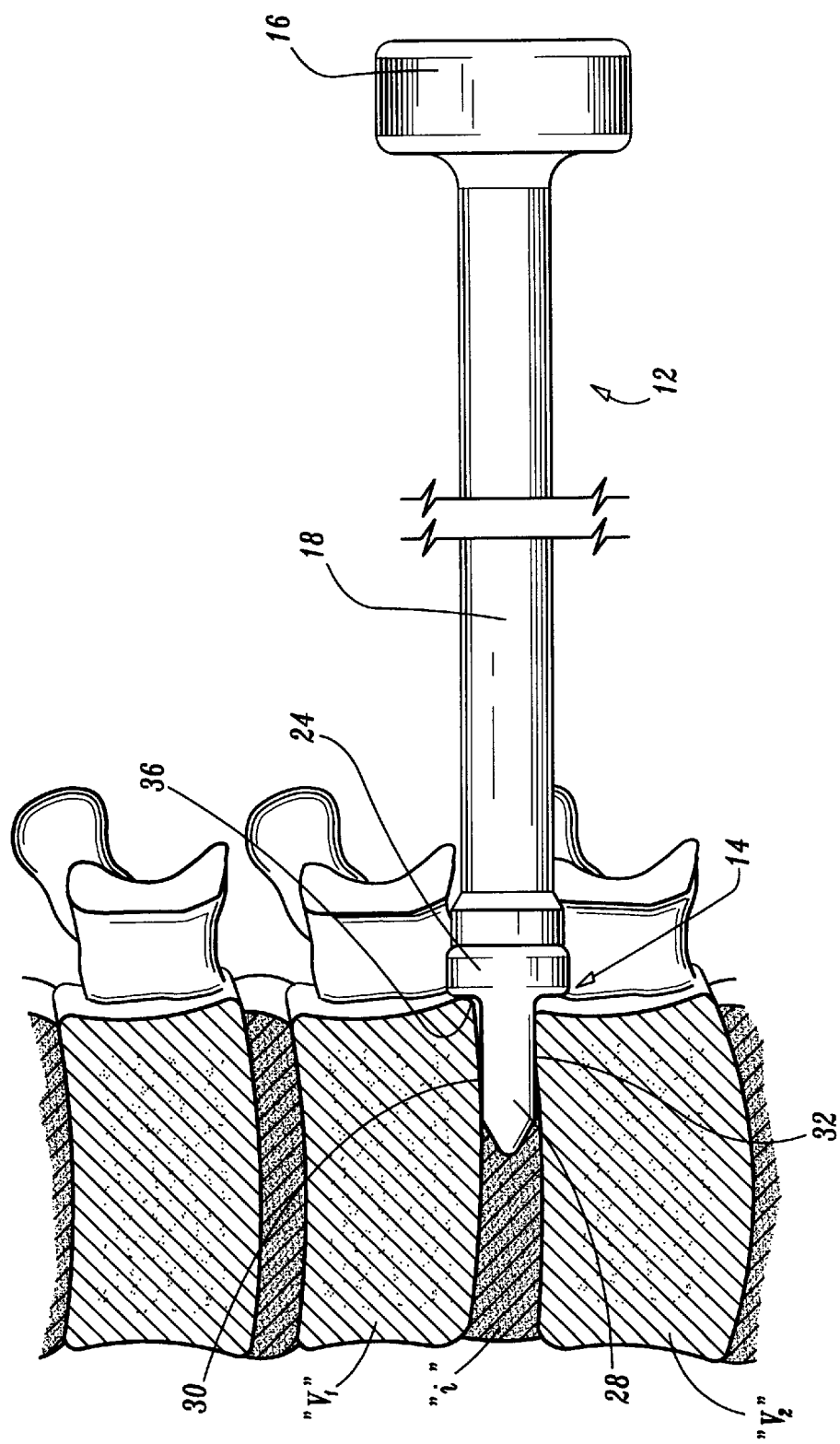
FIG. 5 is a side cross-sectional view of the vertebral column further illustrating positioning of the vertebral spacer apparatus within the intervertebral space.

The intervertebral space is accessed utilizing appropriate retractors, e.g., laminar retractors, dural extractors to expose the posterior vertebral surface. Thereafter, the desired-sized vertebral spacer 14 is selected and mounted to insertion instrument 12 by cooperation of corresponding threaded portions 22,28 of the instrument and the spacer. With reference to FIGS. 4–5, a first lateral side of the intervertebral space "i" is targeted. By manipulating insertion instrument 12, end portion 26 of vertebral spacer 14 is inserted within the intervertebral space "i" adjacent the first lateral side and advanced to a position whereby the abutment surface 36 adjacent trailing end portion 24 engages the posterior margin of the spinal column. As noted above, trailing end portion 24 is strategically sized to prevent entry thereof in the intervertebral space "i". A standard mallet may be utilized to impact handle 16 of instrument 12 to drive vertebral spacer 14 into the disc space. Vertebral spacer 14 is inserted in a manner such that first and second supporting surfaces 30, 32 of each spacer arm 28 respectively engage the opposed vertebral bodies "$V_1$, $V_2$" as depicted in FIG. 5. The arms 28 distract the vertebral end plates in a parallel fashion. Once in position, insertion instrument 12 is removed from vertebral spacer 14 by rotating the instrument 12 to disengage the respective threaded portions 22, 28 thereby leaving the vertebral spacer 14 within the intervertebral space. The spacer arms 28 of vertebral spacer 14 are appropriately dimensioned to stabilize the desired lateral side of the intervertebral space. It is to be noted that vertebral spacer 14 may distract the adjacent vertebrae "$v_1v_2$" as desired to become firmly implanted within the intervertebral space "i".

Figure 6:
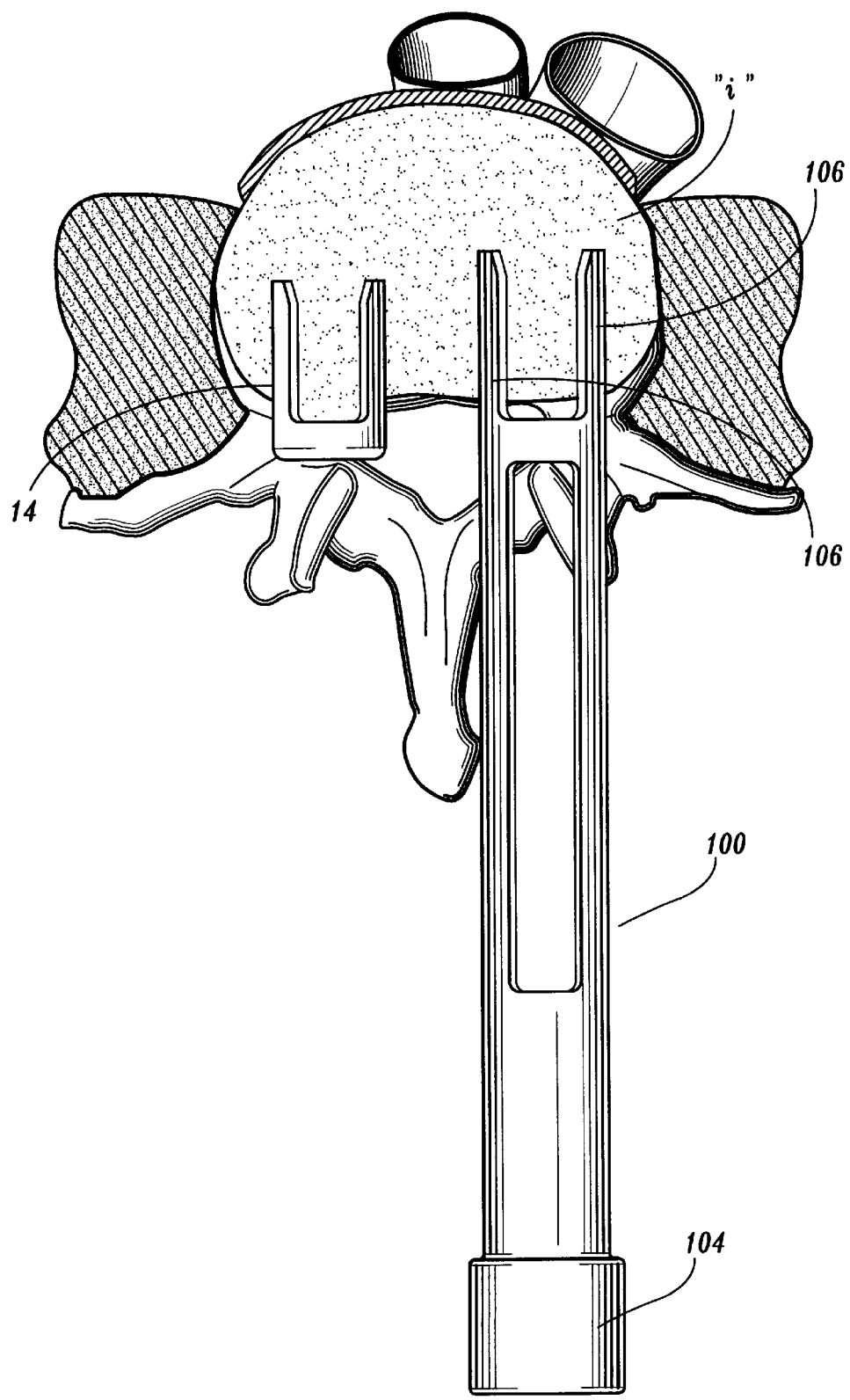
FIG. 6 is a view similar to the view of FIG. 4 illustrating positioning of the vertebral spacer in one lateral side of the intervertebral space and insertion of a surgical retractor in the other lateral side of the space.

With reference now to FIG. 6, retractor 100 is inserted within the intervertebral space "i" adjacent the other lateral side thereof. Retractor 100 may be inserted by placing an impactor cap at the proximal end and impacting the retractor 100 into the intervertebral space "i". In the preferred procedure, retractor 100 is positioned within the intervertebral space "i" such that the first and second supporting surfaces 108, 110 of each retractor arm 106 respectively engage the opposed vertebral bodies "$V_1V_2$". Upon insertion of retractor arms 106, the vertebral bodies "$V_1$ $V_2$" are distracted whereby the retractor arms 100 become firmly lodged within the intervertebral space. The retractor 100 selected preferably corresponds in dimension to the implanted vertebral spacer 14 (i.e., the height of the retractor arms corresponds to the height of the spacer arms) to ensure parallel distraction of the adjacent vertebrae "$V_1$, $V_2$" so as to maintain a predetermined spacial distance of the vertebrae across the span of the intervertebral space "i".

Figure 7:
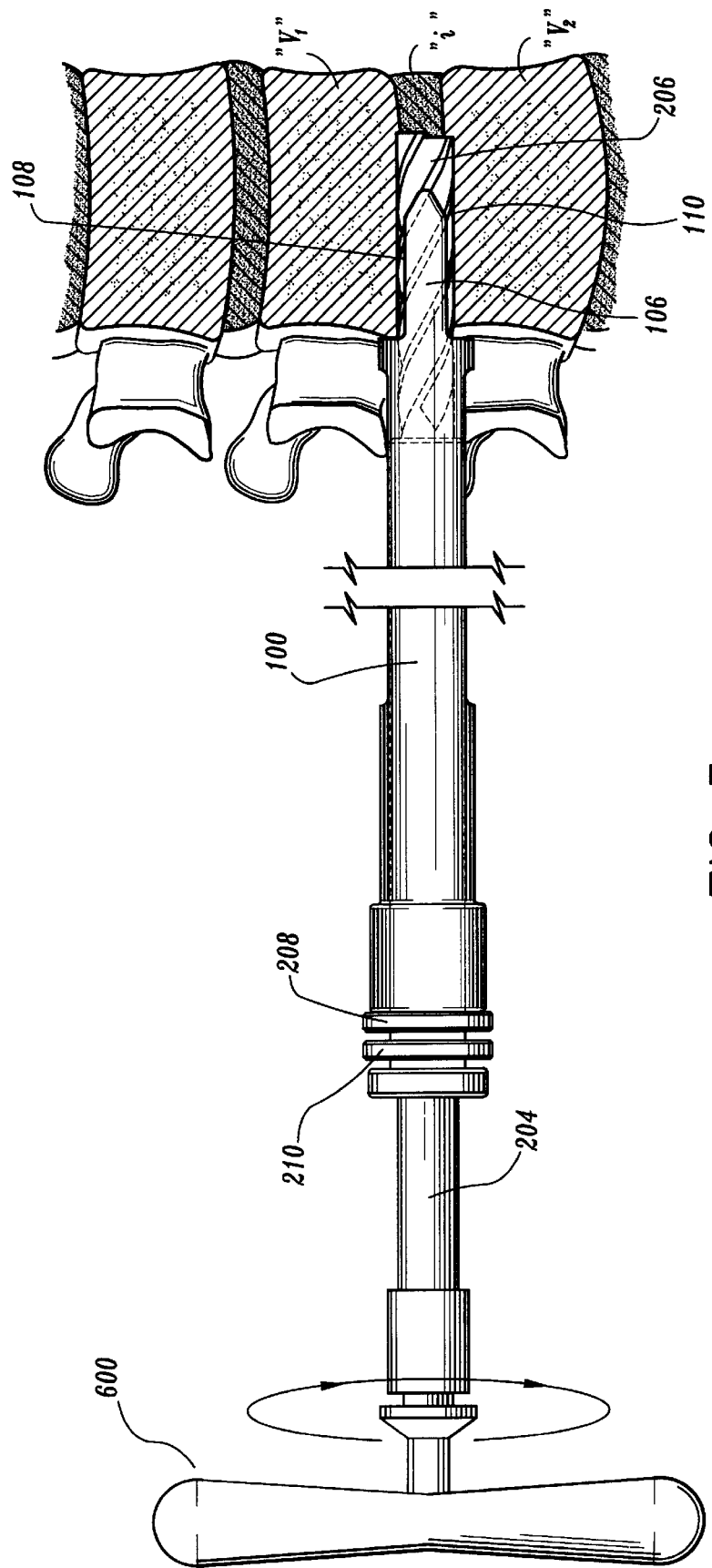
FIG. 7 is a view similar to the view of FIG. 5 illustrating insertion of the drill instrument into the retractor to drill a bore within the adjacent vertebrae.

Referring now to FIG. 7, the surgical drill instrument 300 is now utilized to prepare the disc space and vertebral end plates for insertion of the fusion implant. The cutting depth of drilling instrument is adjusted as desired (i.e., to correspond to the length of the fusion implant) by adjusting collars 208, 210. With the T-handle mounted to surgical drill instrument 300, the instrument is introduced into the axial bore of retractor 100 and advanced to contact the posterior surface of the vertebral bodies, "$V_1V_2$". Drill 200 is advanced into the intervertebral space "i" by rotating T-handle 600 such that drill bit 200 shears the soft tissue and cuts the bone of the adjacent vertebrae "$V_1V_2$" thereby forming a bore which extends into the adjacent vertebrae "V1 $V_2$". Drill 200 is then removed from retractor 100. It is to be noted that during the bore forming process vertebral spacer 14 in conjunction with retractor 100 stabilize the adjacent vertebrae "$V_1$ $V_2$" (e.g., the first lateral side of the intervertebral space is stabilized by spacer 14 and the second lateral side is stabilized by retractor arms 106 of retractor 100) to minimize lateral and/or longitudinal movement of the bodies and also to facilitate the formation of a uniform bore within the end plates.

Figure 8:
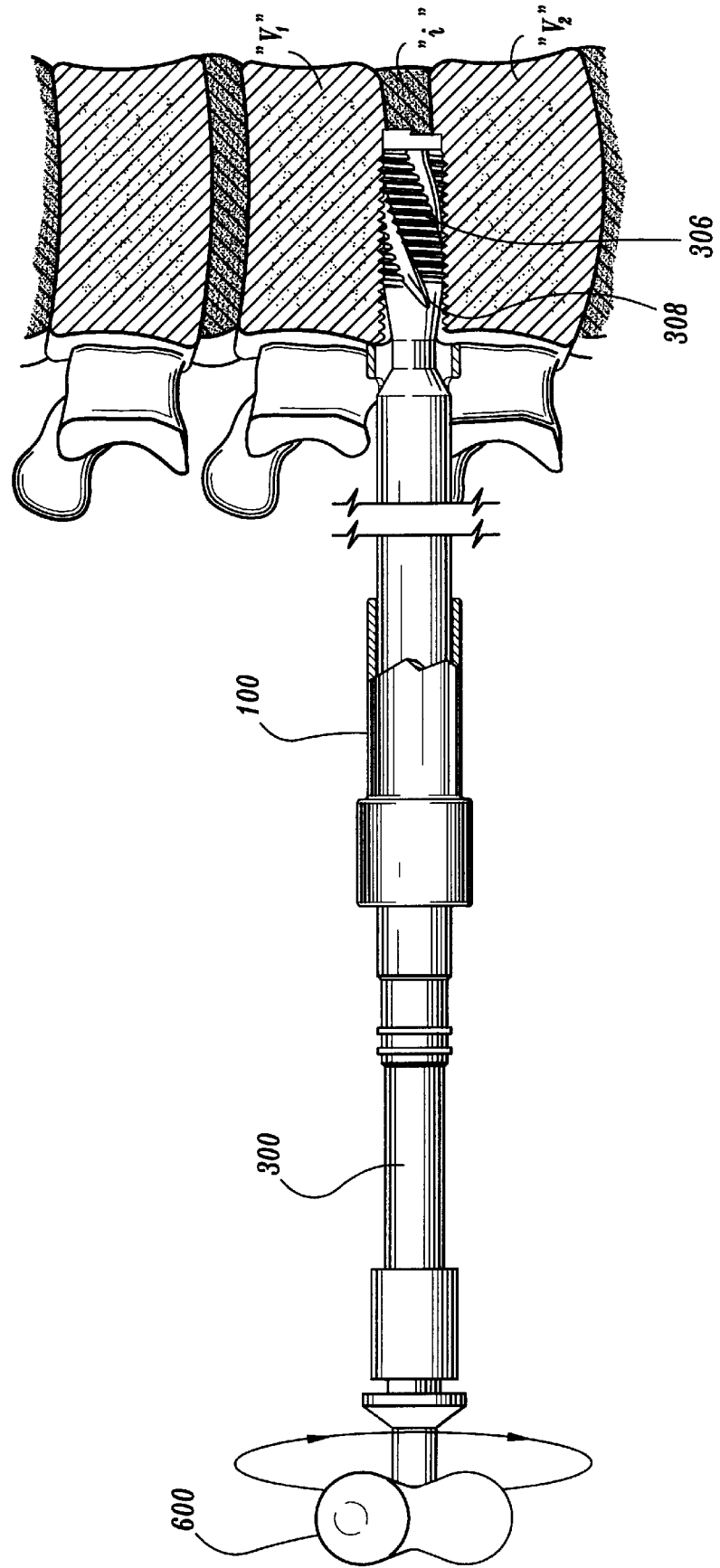
FIG. 8 is a view similar to the view of FIG. 7 illustrating insertion of the tap instrument into the retractor to tap the bore formed by the drill instrument.

Referring now to FIG. 8, tap instrument 300 is selected and attached to the T-handle 600. Tap instrument 300 is inserted into retractor 100 and positioned adjacent the drilled bore formed in the adjacent vertebrae "$V_1V_2$" by the surgical drill 200. With retractor 100 as a direct guide, T-handle 600 is rotated in the direction of the directional arrow of FIG. 8 while simultaneously applying sufficient downward pressure on the T-handle to advance the tap instrument 300 and promote even purchase into the endplates. Upon advancement of the tap instrument 300, the deburred bone chips collect within conveyance channel 308 of tapping head 306, and are conveyed proximally during rotational movement of the tapping head away from the tapping site. Tap instrument 300 is advanced into the bone until the desired depth has been achieved, which occurs when the distal end of tapping head 308 "bottoms out" on the bone. When tap instrument 300 reaches the appropriate depth, the tap instrument 300 is rotated via T-handle 600 in an opposite direction to back the instrument out of the bone.

Figure 9:
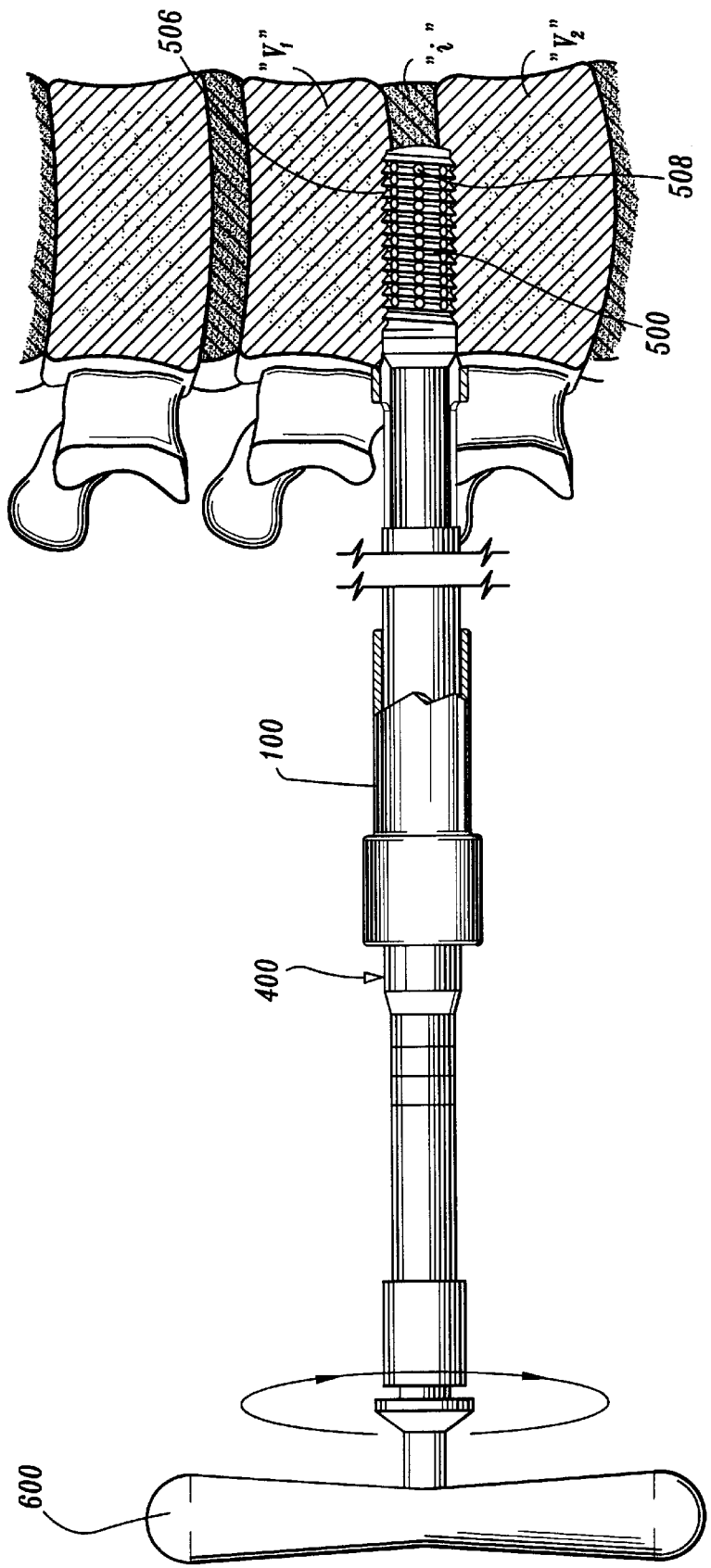
FIG. 9 is a view similar to the view of FIG. 8 illustrating insertion of the implant insertion instrument with mounted implant into the retractor to insert the implant.

With reference now to FIG. 9, attention is focused on the insertion of fusion implant 500. Cage body 502 is mounted onto insertion instrument 400 by positioning the cage body 502 onto mounting portion 408 of the instrument to permit mounting ball 410 to engage one of the apertures of the implant 500. This assembly is attached to T-handle 600. Insertion instrument 400 with mounted cage body 502 is inserted into retractor 100 and the cage body 502 is positioned within the tapped bore by rotating insertion instrument 400 in the direction depicted in FIG. 9. Cage body 502 is advanced until it is completely seated with the bore. An indicator line 414 (FIG. 3) on insertion instrument 400 assists the surgeon in determining when the cage is in proper position. Insertion instrument 400 is then removed from retractor 100.

At this point in the procedure, bone growth inducing substances may be harvested from, e.g., the iliac crest, and packed into the cage body 502 of implant 500 until the cage body 502 is completely filled with bone growth inducing substances. An end cap may then be mounted to the cage body 202. Retractor 100 is then removed.

With implant 500 appropriately positioned in the second lateral side of the intervertebral space "i", attention is directed to preparing the first lateral side for insertion of a second implant. Previously inserted vertebral spacer 14 is removed by insertion of spacer insertion instrument into the operative site and engagement of threaded portion 22 of the instrument with the internal threaded bore 28 of vertebral spacer 14. Once engaged, vertebral spacer 14 is removed by exerting a proximal force on insertion instrument 12.

Thereafter retractor 100 is inserted into the intervertebral space "i" in the area previously occupied by vertebral spacer 14. A second bore is formed in this first lateral side with tapping, if desired, followed by insertion of the implant as effectuated in accordance with the methods and instruments described above in connection with FIGS. 3–8.

Figure 10:
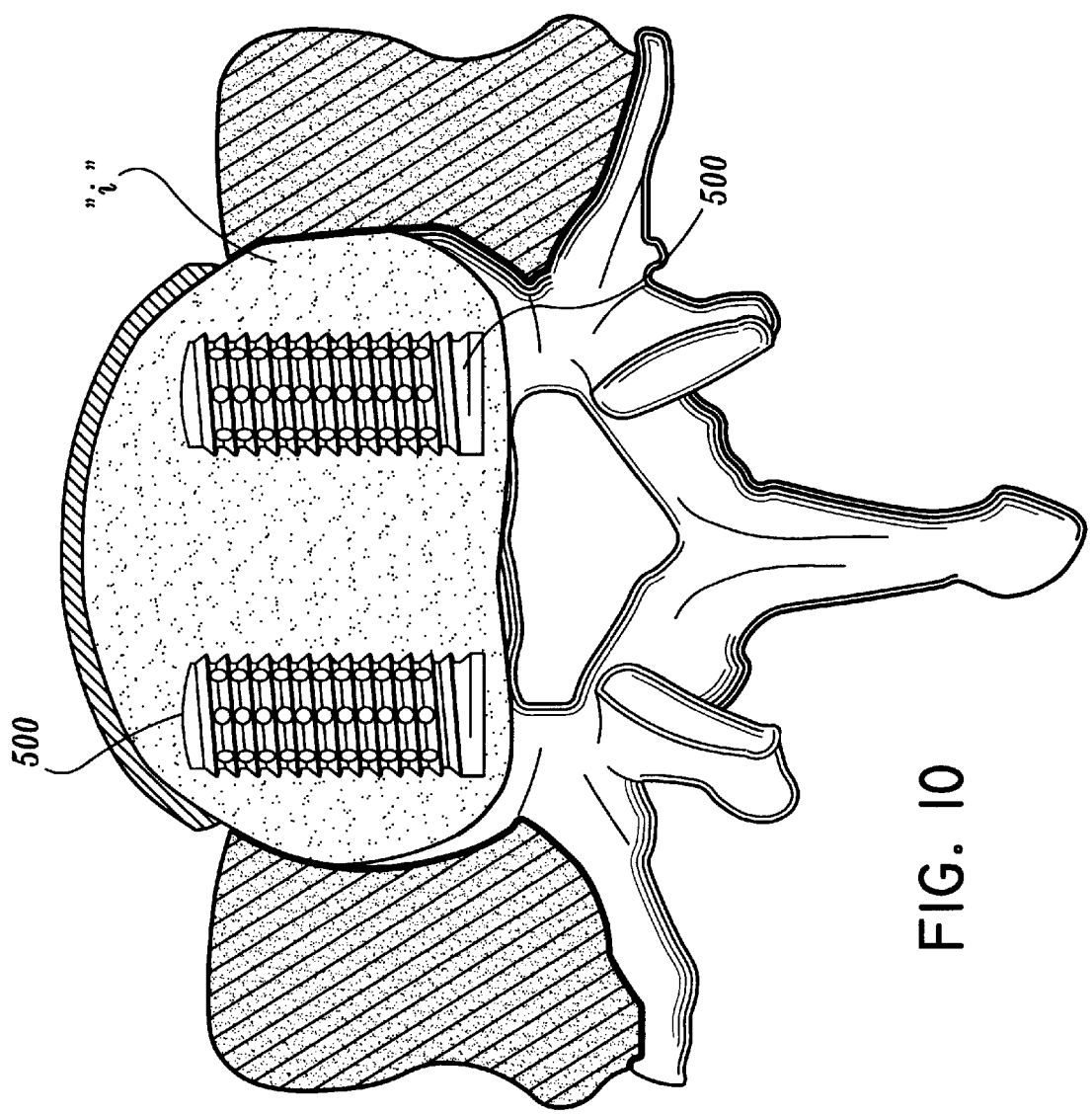
FIG. 10 is a view illustrating insertion of a pair of fusion implants into the intervertebral space.

FIG. 10 illustrates two lateral fusion implants 200 inserted within the intervertebral space.

Referring now to FIGS. 11A–11C, an alternate embodiment of the vertebral spacer of the present disclosure is illustrated. Vertebral spacer 50 is implanted and utilized in a manner substantially similar to vertebral spacer described hereinabove and is inserted with the use of insertion instrument 12. Vertebral spacer 50 includes a solid vertebral spacer body 52 having an insertion end 54 and a trailing end 56. The insertion end 54 has a forward tapered portion 58 defining a generally V-shaped configuration to facilitate insertion within the adjacent vertebrae, and a rear supporting portion 60. The rear supporting portion 60 is of rectangular cross-section and defines upper and lower opposed support surfaces 62, 64 which are illustratively planar to increase surface area contact with the end plates of respective vertebrae upon insertion. The distance between the support surfaces 62,64 preferably approximates the height of the intervertebral space in which vertebral spacer 50 is to be implanted. The support surfaces 62,64 may be knurled, ridged etc. to facilitate retention between the adjacent vertebrae.

Trailing end 56 of spacer body 52 has an enlarged cross-section relative to insertion end 54 to 1) prevent insertion of the trailing end 56 within the intervertebral space and possible undesired contact with, e.g., the aorta, dural nerve, and 2) enhance removal of the vertebral spacer 50 subsequent to implant insertion.

Vertebral spacer body 52 further includes threaded bore 66 adjacent trailing end 56. Threaded bore 66 is engaged by threaded portion 22 of the insertion instrument 12 to mount the vertebral spacer 50 to the instrument 12.

While the above description contains many specifics, these specifics should not be construed as limitations on the scope of the disclosure, but merely as exemplifications of preferred embodiments thereof. For example, it is envisioned that a self-tapping implant may be utilized thus precluding the use of tap instrument 300. Those skilled in the art will envision many other possible variations that are within the scope and spirit of the disclosure as defined by the claims appended hereto.

What is claimed is:

1. A vertebral spacer apparatus, which comprises:

an elongated member having proximal and distal end portions and defining a longitudinal axis; and a vertebral spacer releasably mounted to the elongated member, the vertebral spacer including an insertion end portion and a trailing end portion, the insertion end portion configured to at least span an intervertebral space defined between adjacent vertebrae to supportingly maintain the adjacent vertebrae in predetermined spaced relation, the trailing end portion defining a transverse dimension transverse to the longitudinal axis greater than a corresponding transverse dimension of the insertion end portion and being sized to prevent entry thereof within the intervertebral space, the insertion end portion having a first stationary spacer arm and a second stationary spacer arm, the first and second stationary spacer arms each defining first and second supporting surfaces for respectively engaging the adjacent vertebrae, wherein a dimension defined between the first and second supporting surfaces is sufficient to at least span an intervertebral space defined between adjacent vertebrae.

2. The apparatus according to claim 1 wherein the first and second supporting surfaces are substantially planar to increase surface area contact with adjacent vertebrae.

3. The apparatus according to claim 2 wherein the insertion end portion has a tapered end portion for facilitating insertion into the intervertebral space.

4. The apparatus according to claim 3 wherein the first and second supporting surfaces are in general parallel relation to the longitudinal axis of the elongated member.

5. The apparatus according to claim 4 wherein the trailing end portion defines a rectilinear cross-section.

6. The vertebral spacer according to claim 1 wherein the first and second spacer arms extend in a general longitudinal direction.

7. The apparatus according to claim 6 wherein each spacer arm defines an arm height between the first and second supporting surfaces thereof and the trailing end portion defines a transverse cross-sectional dimension, and wherein the magnitude of the height of each spacer arm is less than the magnitude of the transverse cross-sectional dimension of the trailing end portion.

8. The apparatus according to claim 7 wherein each spacer arm has a tapered end portion for facilitating insertion into the intervertebral space.

9. The apparatus according to claim 8 wherein the first and second supporting surfaces of each spacer arm are in general parallel relation to the longitudinal axis of the elongated member.

10. The apparatus according to claim 8 wherein the trailing end portion defines an arcuate transverse cross-sectional dimension transverse to the longitudinal axis.

11. The apparatus according to claim 1 wherein the elongated member and the vertebral spacer define corresponding threaded portions which cooperatively engage to releasably mount the vertebral spacer to the elongated member.

12. A vertebral spacer apparatus for maintaining a predetermined spacial distance between adjacent vertebrae during implant insertion comprising:

an elongated member having proximal and distal end portions, and defining a longitudinal axis; and a vertebral spacer releasably mounted to the distal end portion of the elongated member, the vertebral spacer including a trailing end portion and an insertion end portion, the trailing end portion sized to prevent entry thereof within the intervertebral space, the trailing end portion having a circular cross-sectional dimension transverse to the longitudinal axis and defining a radius of curvature, the insertion end portion including a pair of opposed stationary arms extending along the longitudinal axis, the stationary arms having arcuate external surfaces extending from the trailing end portion with each external surface defining a radius of curvature substantially equal to the radius of curvature of the trailing end portion, the stationary arms each having a pair of parallel substantially planar upper and lower supporting surfaces for respectively engaging upper and lower vertebrae portions with the adjacent vertebrae to create a temporary span between the adjacent vertebrae.

13. The apparatus according to claim 7 wherein the trailing end portion defines a bearing wall portion extending radially inwardly relative to the first and second retractor arms, the bearing wall portion dimensioned to prevent entry of the trailing end portion within the intervertebral space.

14. The apparatus according to claim 13 wherein the bearing wall portion includes an opening dimensioned to cooperate with the elongated member to mount the vertebral spacer thereto.

* * * * *